United States Patent [19]

Morita et al.

[11] 3,974,390
[45] Aug. 10, 1976

[54] METHOD OF PRODUCING EXCITED STATES OF ATOMIC NUCLEI

[75] Inventors: Masato Morita; Reiko Morita, both of Suita, Japan

[73] Assignee: International Nuclear Fuel Co., Ltd., Osaka, Japan

[22] Filed: Jan. 9, 1974

[21] Appl. No.: 433,911

[30] Foreign Application Priority Data

Jan. 9, 1973 Japan.................................. 48-5765
July 11, 1973 Japan.............................. 48-78141

[52] U.S. Cl............................ 250/492 R; 250/281; 250/282; 250/306; 250/492 B
[51] Int. Cl.² .......................................... G21G 1/00
[58] Field of Search ........... 250/492, 306, 307, 281, 250/282

Primary Examiner—Alfred E. Smith
Assistant Examiner—B. C. Anderson
Attorney, Agent, or Firm—Stewart and Kolasch, Ltd.

[57] ABSTRACT

A method of producing excited states of atomic nuclei which comprises bombarding atoms with X rays or electrons, characterized in that (1) in the atoms selected to be produced in the excited state of their nuclei, (a) the difference between the nuclear excitation energy and the difference between the binding energies of adequately selected two electron orbits is small enough to introduce the nuclear excitation by electron transition, and (b) the system of the nucleus and the electrons in the case of ionizing an orbital electron in said atoms should satisfy the spin and parity conservation laws, and (2) the energy of the bombarding X rays or electrons should be larger than the binding energy of one of the said two electron orbits which is located at shorter distance from the atomic nucleus. According to the present invention, atomic nuclei can be excited in a relatively simple manner without requiring the use of large scale apparatus, equipment and production facilities, e.g., factories. It is also possible to produce radioactive substances or separate a particular isotope with an extremely high purity from a mixture of isotopes by utilizing nuclear excitation.

5 Claims, No Drawings

METHOD OF PRODUCING EXCITED STATES OF ATOMIC NUCLEI

BACKGROUND OF THE INVENTION

The present invention relates to a method of producing excited states of atomic nuclei. More particularly, the present invention relates to a method of producing excited states of atomic nuclei, which comprises bombarding atoms with X rays or electrons under specific conditions.

In general, the excited states of atomic nuclei capable of radiating gamma rays or internal conversion electrons may exist usually as doughter nuclei of radioactive nuclides emitting alpha or beta rays. In conventional methods, artificial production of such excited states of atomic nuclei necessitated the use of large scale apparatus and factories such as a nuclear reactor and other incidental large equipment for preparing radioactive nuclides. It is also possible to produce the excited states of atomic nuclei as residual nuclei by bombarding adequately selected target nuclei with nucleons accelerated by a cyclotron, a Van de Graaff accelerator or the like to cause nuclear reactions. The number of the residual nuclei produced in this method is, however, extremely small and the disadvantage of the necessity to use large apparatus, equipment and production facilities, e.g., factories as in the case of using nuclear reactors, is overcome by the present method.

BRIEF SUMMARY OF INVENTION

It is an object of the present invention to provide a method of producing excited states of atomic nuclei in a comparatively simple manner without necessity of using large scale apparatus and equipments.

It is another object of the present invention to provide a method of producing excited states of atomic nuclei by bombarding atoms with X rays or electrons under specific conditions established for both the atoms to be bombarded and the energy of bombarding (irradiating) X rays or electrons.

It is still another object of this invention to provide a method of producing radioactive substances by utilizing the production of excited states of atomic nuclei.

It is a further object of this invention to provide a method of separating a particular isotope from a mixture of isotopes by utilizing the production of such excited states of atomic nuclei.

Other objects, features and advantages of the present invention will become apparent as the description proceeds.

DETAILED DESCRIPTION OF THE INVENTION

It has now been found surprisingly that excited states of atomic nuclei can be produced in a comparatively simple manner by bombarding atoms with X rays or electrons under specific conditions without the necessity of using large scale apparatus, equipments and production facilities, e.g., factories as in the conventional methods.

In accordance with the present invention, therefore, there is provided a method of producing excited states of atomic nuclei which comprises bombarding atoms with X rays or electrons, characterized in that (1) in the atoms selected to be produced in the excited state of their nuclei, (a) the difference between the nuclear excitation energy and the difference between the binding energies of adequately selected two electron orbits is small enough to introduce the nuclear excitation by electron transition, and (b) the system of the nucleus and the electrons in the case of ionizing an orbital electron in said atoms should satisfy the spin and parity conservation laws, and (2) the energy of the bombarding X rays or electrons should be larger than the binding energy of one of the said two electron orbits which is located at the shorter distance from the atomic nucleus.

The method of the present invention is based on the technical idea quite different from that in the prior art techniques and is an epoch-making excellent method for producing nuclear excitation that is utterly unexpected from the knowledge of the art, even by those skilled in the art. In the prior art methods, production of excited states of atomic nuclei is carried out by the conversion of nuclides (nuclear transmutation) in the nuclear reactions. In contrast to this, the method of this invention is not directed to such conversion of nuclides but to merely raising the energy of atomic nuclei from the ground state to the excited state. The production of the excited state of atomic nuclei as contemplated in the present invention by utilizing bombardment with X rays or electrons, i.e. a physical means in a low energy region, such as the use of an electron gun or an X-ray tube, is a novel and important finding and is not at all anticipatory from the knowledge in the prior art.

An atom consists of an atomic nucleus and bound electrons the number of which is equal to the atomic number Z. When the atom is bombarded with X rays or electrons, the incoming energy of which is higher than the binding energy of an orbital electron, this orbital electron is ejected from the atom. Since the binding energy is different for every orbit, an electron of a particular orbit can selectively be kicked off by adjusting the energy of the X rays or electron to make an electron hole artificially for the relevant electron orbit. If the electron hole is made in a closed shell, the state of the atom becomes energetically unstable so that an electron of an outer orbit will immediately jump into the hole. In this electron transition, the energy corresponding to the difference between the binding energies of these two orbits is emitted in the form of X rays out of the atom. With a certain probability, this energy is transferred to an electron belonging to a far more outer orbit to let the electron overcome its binding energy and go out of the atom. This is called the Auger electron emission.

It has now been found, however, that when such electron hole is created in the closed shell (orbit) by bombardment of atoms with X rays or electrons, the excess energy in the subsequent electron transition is transferred to the nucleus, in competition with said well-known X-ray and Auger electron emissions, and the nucleus is excited by this energy absorption from its ground state to an excited state. This new surprising phenomenon found by the present inventors is called "Nuclear Excitation by Electron Transition", which is referred to herein simply as "nuclear excitation". By the way, this phenomenon may be called "Dynamic Excitation of Atomic Nucleus by Electron Transition" or "Inverse Internal Conversion Process".

According to one embodiment of this invention, the excited states of atomic nuclei can be produced in a simple manner without necessity of using large scale apparatus, for example, atomic piles as used in the prior art techniques.

By bombarding atoms with the X rays or electrons, this phenomenon can take place only if the following specific conditions are fulfilled:

1. In order to produce the excited state of the nuclei,
   a. the relevant atoms have such a pair of the electron orbits that the difference between the nuclear excitation energy and the binding energy difference of these two orbits is small enough to introduce the nuclear excitation by electron transition, and
   b. the system of the nucleus whose atomic number is represented by Z and the (Z−1) electrons should satisfy the spin and parity conservation laws for the above pair of electron orbits and the nuclear ground and excited states.
2. The energy of the bombarding X rays or electrons should be larger than the binding energy of the electron which is more tightly bound with the nucleus among the above two orbits.

These conditions will be explained hereinafter by way of formulas wherein $I_g$ stands for the spin of the nucleus in the ground state, $\pi_g$ for the parity thereof, $\psi_g$ for the wave function thereof, $I_e$ for the spin of the same nucleus in the excited state, $\pi_e$ for the parity thereof, $\psi_e$ for the wave function thereof, $E_N$ for the excitation energy thereof, $\phi_1$ for the wave function of an electron in the closed shell (orbit) which will be kicked off to form an electron hole by bombardment with X rays or electrons, $J_1$ for the spin thereof, $\pi_1$ for the parity thereof, $E_1$ for the binding energy thereof, $\phi_2$ for the wave function of an electron in the outer shell which will jump into the electron hole in the orbit $\phi_1$, $J_2$ for the spin thereof, $\pi_2$ for the parity thereof, and $E_2$ for the binding energy thereof.

The condition required for energies can be expressed by $$E_N \approx E_1 - E_2.$$

The interaction energy $E_i$ of the system of the nucleus and an electron is expressed quantum mechanically by the non-diagonal element of a matrix $$E_i = (\psi_e \phi_1 |H_i| \psi_g \phi_2)$$

wherein $H_i$ is the Hamiltonian of the electromagnetic interactions of the system.

More particularly, in the energy conditions, the probability of the nuclear excitation depends on $$\frac{E_i}{E_N - (E_1 - E_2)}$$

By expressing the above quantity as $x$, the case where a large absolute value of $x$ is preferable. In many cases, the absolute value of $x$ is however smaller than unity. By denoting the value of $x$ for a particular isotope of a given element as $x_0$, the nuclear excitation can take place only for the isotope with $x_0$ if the other isotopes of the same element have $x$'s the values of which are less than about $0.1x_0$.

In many elements, $x$'s are actually less than $0.001x_0$ for the isotopes except for a particular isotope with $x_0$. (This means that the energy conditions, $E_N \approx E_1 - E_2$, is not satisfied for these isotopes.) Accordingly, various practical applications of the method of this invention as will be given hereinafter can be performed without difficulty even though the value of $x_0$ itself is relatively small.

Next, the spin (or angular momentum) of the system of the nucleus and an electron should satisfy the conservation law for the spin vectors.

$$\vec{I}_g + \vec{J}_1 = \vec{I}_e + \vec{J}_2$$

wherein the quantities expressed by the symbols with arrow are spin vectors for the physical states which have spin values expressed by corresponding regular symbols, respectively. The parity of the system of the nucleus and electron should also satisfy the parity conservation law:

$$\pi_g \pi_1 = \pi_e \pi_2.$$

In the nucleus of an atom of the atomic number Z which has an electron hole in a certain electron orbit and is thus surrounded by the (Z−1) orbital electrons, the conditions above described are given for the case where the (Z−1) orbital electrons can be represented by a single electron wave function corresponding to the orbit where the electron hole is made. More generally, the above conditions should be fulfilled by the resultant system of the nucleus and the (Z−1) electron system. In this case, $\phi_1$ and $\phi_2$ should be replaced by $\Phi_1$ and $\Phi_2$, respectively, where $\Phi_1$ and $\Phi_2$ stand for wave functions of the (Z−1) electron system before and after the electron transition. In the expression of $E_i$, $\phi_1$ should be replaced by $\Phi_2$ and $\phi_2$ by $\Phi_1$, due to the difference of the electron and its hole state.

It is necessary to produce the electron hole in an orbit for which the binding energy of the electron is $E_1$. It will easily be understood therefore that in the method of this invention the energy of the X rays or electrons for bombarding atoms should be larger than $E_1$. If this energy is less than $E_1$, the excited states of the nuclei of the relevant atoms will not be produced.

In fact, a small disk of metallic osmium having no radioactivity was bombarded with electrons from an electron gun and measured at every definite time interval, using a GM counter. Internal conversion electrons were then observed to prove that the first excited state of Osmium 189 was produced according to the method of this invention.

According to another embodiment of this invention, radioactive substances can be produced in a very simple manner. Atomic nuclei are deexcited from the excited state to the ground state by emitting gamma rays or internal conversion electrons, a material involving these atomic nuclei in such excited state are very useful as radioactive substance. In accordance with this embodiment, radioactive substances can be produced easily by employing, under the above mentioned specific conditions, an X-ray or electron generator such as X-ray tube or electron gun widely used in this art without necessity of a large scale apparatus such as nuclear reactor. It will be understood that the production of atomic nuclei in an excited state attains at the same time the production of radioactive substance. In the method of the present invention, the atomic nuclei are excited in their excited states and subsequently these states are deexcited by emitting gamma rays or internal conversion electrons. That is, these atomic nuclei in their excited states can be considered as radioactive substance having a relatively short life of radioactivity. Consequently this method enables the artificial production of radioactive substances.

According to still another embodiment of this invention, a particular isotope can selectively be separated from a mixture of isotopes by utilizing nuclear excitation. It is known that when the atomic nuclei of a certain isotope are in the excited state, such isotope can be separated by a chemical means. In the prior art techniques, however, it was necessary to use radioactive parent nuclei or adequately selected target nuclei for producing atomic nuclei in such excited state. Accordingly, large scale apparatus or equipment was required in the prior art techniques for producing such radioactive nuclei. Atomic nuclei in the excited state which are easily produced in the method of the present invention from their ground state can be separated chemically by one of the methods known in the prior art. In contrast, the methods currently adopted for separating uranium 235 from a mixture of uranium isotopes is possible only by physical means such as contrifugal separation or diffusion, utilizing the difference in mass among the isotopes.

More precisely, an atomic nucleus in the excited state emits a gamma rays and is then deexcited to the ground state whereby the deexciting atomic nucleus is recoiled in the direction opposite to the direction of the emitted gamma ray according to the law of conservation of momentum. When a chemical bond is formed between an atom having a nucleus in the excited state and the other atom or atoms, the chemical bond(s) are disconnected by the movement of the atomic nucleus to make the former atom ionized, thus differentiating it in the chemical state from the other isotopes originally in the ground state. Accordingly, isotopes can be separated chemically. In this manner, only atoms of a desired isotope once kept in the excited state are chemically collectable. Atoms failing to be in the nuclear excited state cannot be separated even if they are the same nuclide.

A chemical method for separating isotopes is known as the Szilard-Chalmers method reported by L. Szilard and T. A. Chalmers, which relates to concentration of free radioactive iodine 128 by bombarding ethyl iodide with neutrons followed by extraction with water (Nature 134 (1934), 494 and 642). This method is well-known in the field of radiochemistry and generally teaches that atoms having radioactive nuclei (precisely, their doughter nuclei), residual nuclei of nuclear reactions, long-life nuclear isomers and the like can be separated by a chemical means. Especially in the case of isomers emitting internal conversion electrons in addition to gamma rays, they become devoid of their orbital electron and are kept in ionized state when deexcited to the ground state. Thus, they are differentiated from atoms not undergoing nuclear excitation and separated therefrom by suitable chemical means including the use of a precipitating agent if the isotopes in the ionized state form insoluble solid precipitates with such agent. In general, such chemical means will easily be selected by those skilled in the art, with considering the nature of the isotopes in the ionized state. The atoms in the ionized state can also be separated electrochemically; if atoms to be separated are in gaseous state, they can be collected easily by passing them through an electrically charged screen.

Since isotopes can thus be separated chemically as far as their atomic nuclei are brought into the excited state, the method of this invention can be utilized for chemical separation of isotopes by converting the nuclear ground state of isotopes to be separated, to their excited state, i.e. raising energy of their atomic nuclei.

As a preferable example in practice of this invention, a method of separating uranium 235 alone from a mixture of several uranium isotopes is described as follows: For the first excited state of uranium 235, which has a very low excitation energy, there is a pair of electron orbits satisfying $E_N \approx E_1 - E_2$. The interaction energy $E_i$ is, however, too small. Therefore, the second excited state of 13.1 kilo-electron-volts is selected. In this case, a pair of the electron orbits which satisfy the previously described conditions are $2p_{3/2}$ and $3d_{3/2}$. Their beinding energies are 17.168 and 3.728 kilo-electron-volts, respectively. Therefore, $E_1 - E_2 = 13.440$ kilo-electron-volts which is nearly equal to the nuclear excitation energy $E_N = 13.1$ kilo-electron-volts. Uranium isotopes other than uranium 235 can never be excited since the excitation energies of their first nuclear excited states are about 40 kilo-electron-volts and there are no pair of electron orbits satisfying the condition $E_N \approx E_1 - E_2$. Accordingly, uranium 235 alone can selectively be separated from the uranium isotopes. For this purpose, a mixture of uranium isotopes is bombarded with X-rays or electrons having an energy of at least 17.2 kilo-electron-volts to produce an electron hole in the $2p_{3/2}$ electron orbit of uranium atoms. The electron hole is then filled up with the $3d_{3/2}$ electron whereby the second excited state of uranium 235 is produced. This state decays immediately by emission of a gamma ray or an internal conversion electron to produce the first excited state of 26-minute halflife. The isotope mixture thus treated is then subjected to any suitable chemical procedure to separate uranium 235 from the mixture. In this manner, uranium 235 having an extremely high purity up to 100 % can be obtained.

The foregoing example illustrates only the case of separating uranium 235 from a mixture of various uranium isotopes. The method of this invention can also be applied to the separation of nuclides so far as they satisfy the requirements (1)-(a) and (1)-(b) recited hereinbefore for nuclear excitation. Examples of other nuclides to which the method of this invention is applicable include osmium 189, neptunium 237, gold 197, iridium 193, tantalum 181, dysprosium 161 and tin 119.

In contrast to the prior art methods of separating uranium 235 where the physical means such as diffusion and centrifugal separation, the method of this invention in combination with a suitable chemical procedure enables the separation of a certain kind of isotope, for example uranium 235 as illustrated above, in an extremely high purity up to 100 % from a mixture of isotopes of the same element. Therefore, this invention has outstanding merits also in respect of purity of the isotope obtained in isotope separation as an application of this invention.

The method of this invention for producing excited states of atomic nuclei is based on an entirely new technical consideration and is an epoch-making even from the pure scientific point of view. The utilization of this invention finds therefore many valuable applications to a variety of industrial fields. Firstly, the method of this invention makes it possible to produce radioactive substances in a very simple manner. Since the atomic nuclei in the excited state emit gamma rays or internal conversion electrons when deexcited to the ground state, they can be used in place of known radioactive isotopes utilizable in various industrial fields, medical fields for diagnosis and therapy of patients and agricultural and the like fields. As the radioactive substances produced by the method of this invention include those having a relatively short life in emission of radioactive rays, these substances are useful especially in the cases where such specific nature is demanded. Secondly, the method of this invention enables the selective separation of a specific isotope from a mixture of isotopes. In this aspect, the method of this invention is extremely valuable for separating uranium 235 alone from a mixture of uranium isotopes and thus brings about inestimable merits in the fields utilizing uranium 235 of high purity.

What is claimed is:

1. A method of producing excited states of atomic nuclei which comprises bombarding atoms with X rays or electrons, characterized in that
   1. in the atoms selected to be produced in the excited state of their nuclei,
      a. the difference between the nuclear excitation energy and the difference between the binding energies of adequately selected two electron orbits is small enough to introduce the nuclear excitation by electron transition, and
      b. the system of the nucleus and the electrons in the case of ionizing an orbital electron in said atoms should satisfy the spin and parity conservation laws, and
   2. the energy of the bombarding X rays or electrons should be larger than the binding energy of one of the said two electron orbits which is located at the shorter distance from the atomic nucleus.

2. A method according to claim 1 wherein the atoms having nuclei to be excited are those of uranium 235.

3. A method of producing radioactive substances by nuclear excitation which comprises bombarding a substance with X rays or electrons, characterized in that
   1. in the atoms of the substance selected to be bombarded,
      a. the difference between the nuclear excitation energy and the difference between the binding energies of adequately selected two electron orbits is small enough to introduce the nuclear excitation by electron transition, and
      b. the system of the nucleus and the electrons in the case of ionizing an orbital electron in said atoms should satisfy the spin and parity conservation laws, and
   2. the energy of the bombarding X rays or electrons should be larger than the binding energy of one of the said two electron orbits which is located at the shorter distance from the atomic nucleus.

4. A method of separating a specific isotope from a mixture of isotopes of the same element by means of nuclear excitation, which comprises bombarding the mixture with X rays or electrons and then subjecting the bombarded isotopes to a chemical treatment using one or more chemical reagents or an electrochemical treatment using electrically charged materials thereby separating the ionized specific isotope from the mixture of isotopes, characterized in that
   1. in the atoms of the isotope to be separated,
      a. the difference between the nuclear excitation energy and the difference between the binding energies of adequately selected two electron orbits is small enough to introduce the nuclear excitation by electron transition, and
      b. the system of the nucleus and the electrons in the case of ionizing an orbital electron in said atoms should satisfy the spin and parity conservation laws, and
   2. the energy of the bombarding X rays or electrons should be larger than the binding energy of one of the said two electron orbits which is located at shorter distance from the atomic nucleus.

5. A method according to claim 4 wherein uranium 235 is separated from a mixture of uranium isotopes.

* * * * *